United States Patent
Hester et al.

(10) Patent No.: US 9,314,245 B2
(45) Date of Patent: Apr. 19, 2016

(54) SURGICAL FASTENERS AND METHODS AND DEVICES FOR DEPLOYING A SURGICAL FASTENER

(75) Inventors: Douglas Hester, Raynham, MA (US); Joyce-Marie Gallagher, Boston, MA (US)

(73) Assignee: DePuy Mitek, LLC, Raynham, MA (US)

(*) Notice: Subject to any disclaimer, the term of this patent is extended or adjusted under 35 U.S.C. 154(b) by 635 days.

(21) Appl. No.: 13/492,171

(22) Filed: Jun. 8, 2012

(65) Prior Publication Data

US 2013/0331839 A1 Dec. 12, 2013

(51) Int. Cl.

| A61B 17/56 | (2006.01) |
|---|---|
| A61B 17/58 | (2006.01) |
| A61B 17/064 | (2006.01) |
| A61B 17/84 | (2006.01) |
| A61F 2/30 | (2006.01) |
| A61B 17/068 | (2006.01) |
| A61B 17/00 | (2006.01) |

(52) U.S. Cl.
CPC ......... *A61B 17/0642* (2013.01); *A61B 17/0682* (2013.01); *A61B 2017/00867* (2013.01)

(58) Field of Classification Search
CPC ............. A61B 17/064; A61B 17/0642; A61B 17/0682
USPC ........................................... 606/75, 916, 219
See application file for complete search history.

(56) References Cited

U.S. PATENT DOCUMENTS

| 5,667,527 A * | 9/1997 | Cook ............................ 606/219 |
|---|---|---|
| 6,626,916 B1 | 9/2003 | Yeung et al. |
| 7,547,315 B2 | 6/2009 | Peterson et al. |
| 2005/0080454 A1* | 4/2005 | Drews et al. .................. 606/221 |
| 2006/0282118 A1 | 12/2006 | Surti |
| 2008/0065154 A1 | 3/2008 | Allard et al. |
| 2009/0272786 A1 | 11/2009 | Zeiner et al. |
| 2010/0116867 A1 | 5/2010 | Balbierz et al. |

FOREIGN PATENT DOCUMENTS

WO 2008/022261 A2 2/2008

OTHER PUBLICATIONS

[No Author Listed] OmniSpan: Prominent in Stength, Subtle in Profile. DePuy Mitek Inc. 2010, 4 pages. Product information.
Extended European Search Report for Application No. 13171277.0 issued Dec. 12, 2013 (7 Pages).

* cited by examiner

*Primary Examiner* — David Bates
*Assistant Examiner* — Olivia C Chang (57) ABSTRACT

Various exemplary surgical fasteners are provided, and methods and devices are provided for deploying a surgical fastener. In general, the methods and devices allow a surgical fastener to be deployed to secure tissue to bone. In one embodiment, a surgical fastener can be configured to move between a first linear or compressed configuration, in which the fastener can have a first maximum diameter, and a second bent or expanded configuration, in which the fastener can have a second maximum diameter greater than the first maximum diameter. A delivery device can be configured to advance the fastener through tissue and into bone to attach the tissue to the bone. The delivery device can be configured to maintain the fastener in the compressed configuration such that when the fastener is released from the delivery device, the fastener can be configured to self-expand from the compressed configuration to the expanded configuration.

22 Claims, 4 Drawing Sheets

SURGICAL FASTENERS AND METHODS AND DEVICES FOR DEPLOYING A SURGICAL FASTENER

FIELD OF THE INVENTION

The present invention relates generally to surgical fasteners and methods and devices for deploying a surgical fastener, and in particular to pre-bent surgical fasteners and methods for use.

BACKGROUND OF THE INVENTION

The complete or partial detachment of ligaments, tendons, and/or other soft tissues from their associated bones within the body are relatively commonplace injuries, particularly among athletes. Such injuries are generally the result of excessive stresses being placed on these tissues. By way of example, tissue detachment may occur as the result of an accident such as a fall, over-exertion during a work-related activity, during the course of an athletic event, or in any one of many other situations and/or activities.

In the case of a partial detachment, the injury will frequently heal itself, if given sufficient time and if care is taken not to expose the injury to further undue stress. In the case of complete detachment, however, surgery may be needed to re-attach the soft tissue to its associated bone or bones. Numerous devices are currently available to re-attach soft tissue to bone. Examples of such currently-available devices include screws, staples, suture anchors, and tacks.

Tissue may be attached to bone during traditional open surgery or during minimally invasive, e.g., arthroscopic, surgical procedures. Minimally invasive surgical procedures are usually preferred over open surgery since they are less invasive, are less likely to cause patient trauma, and can reduce patient recovery time. In a minimally invasive surgical procedure, the surgeon performs diagnostic and therapeutic procedures at the surgical site through one or more small incisions. Reducing the size and number of incisions is desirable because it can reduce patient trauma and recovery time. However, in surgical procedures involving tissue reattachment, the size of the incision can be undesirably large in order to deliver a fastener of adequate size and strength to secure tissue. In addition, applying multiple fasteners can be time consuming and cumbersome because the device delivering the fasteners may need to be removed from a patient after delivery of each fastener for loading of a new fastener to be delivered.

Accordingly, there remains a need for improved surgical fasteners and methods and devices for deploying a surgical fastener.

SUMMARY OF THE INVENTION

The present invention generally provides surgical fasteners and methods and devices for deploying a surgical fastener. In one embodiment, a surgical method is provided that includes positioning a distal end of a cannula adjacent to a tissue overlying a bone and advancing a first leg of a fastener from the distal end of the cannula to drive the first leg through the tissue and into the bone. After advancing the first leg, the distal end of the cannula is repositioned relative to the tissue. After repositioning the distal end of the cannula, a second leg of the fastener is advanced from the distal end of the cannula to drive the second leg through the tissue and into the bone, thereby attaching the tissue to the bone.

Repositioning the distal end of the cannula can include moving the distal end of the cannula such that a back span of the fastener extending between the first and second legs pivots relative to the first leg. The fastener can be formed from a shape memory material such that the back span is biased to pivot when the distal end of the cannula is repositioned relative to the tissue. In some embodiments, repositioning the distal end of the cannula can cause an intermediate portion of the fastener extending between the first and second legs of the fastener to extend through an opening formed in a sidewall of the cannula.

The method can have any number of variations. For example, advancing the first leg of the fastener can include advancing the first leg of the fastener along a longitudinal axis of the cannula to pass the first leg of the fastener out of the cannula, and repositioning the distal end of the cannula can include moving the cannula in a direction transverse to the longitudinal axis of the cannula. For another example, advancing the first leg of the fastener can include driving a pusher distally through the cannula to push the first leg of the fastener through the tissue and into the bone, and advancing the second leg of the fastener can include driving the pusher distally through the cannula to push the second leg of the fastener through the tissue and into the bone.

In another embodiment, a surgical method is provided that includes advancing a first end of a fastener longitudinally through an inner passageway of an elongate member to pass the first end out of the inner passageway, through a tissue of a patient, and into a bone underlying the tissue. After advancing the first end of the fastener, the elongate member can be moved laterally relative to the tissue, thereby moving a second end of the fastener located within the inner passageway laterally relative to the tissue and thereby causing an intermediate portion of the fastener extending between the first and second ends of the fastener to extend through an opening formed in a sidewall of the elongate member. After moving the elongate member, the second end of the fastener can be advanced longitudinally through the inner passageway of the elongate member to pass the second end out of the inner passageway, through the tissue, and into the bone underlying the tissue.

In some embodiments, after advancing the second end of the fastener, a first end of a second fastener can be advanced longitudinally through the inner passageway of the elongate member to pass the first end of the second fastener out of the inner passageway, through a tissue of a patient, and into a bone underlying the tissue. After advancing the first end of the second fastener, the elongate member can be moved laterally relative to the tissue, thereby moving a second end of the second fastener located within the inner passageway to move laterally relative to the tissue and thereby causing an intermediate portion of the second fastener extending between the first and second ends of the second fastener to extend through the opening formed in the sidewall of the elongate member. After moving the elongate member, the second end of the second fastener can be advanced longitudinally through the inner passageway of the elongate member to pass the second end of the second fastener out of the inner passageway, through the tissue, and into the bone underlying the tissue.

The method can have a number of variations. For example, moving the elongate member laterally can cause the intermediate portion to pivot such that the intermediate portion extends through the opening formed in the sidewall of the cannula. For another example, after advancing the second end of the fastener, the elongate member can be moved longitudinally to remove the elongate member from a body of the patient, thereby leaving the fastener implanted within the patient. For yet another example, advancing the first end of the fastener longitudinally can include driving a pusher distally through the inner passageway of the elongate member to push the first end of the fastener through the tissue and into the bone, and advancing the second end of the fastener longitudinally can include driving the pusher distally through the inner passageway of the elongate member to push the second end of the fastener through the tissue and into the bone. For still another example, advancing the first end of the fastener longitudinally to push the first end of the fastener through the tissue and into the bone and advancing the second end of the fastener longitudinally to push the second end of the fastener through the tissue and into the bone can cause the fastener to move from an initial substantially straight configuration to a final U-shaped configuration.

In another embodiment, a cannula has a fastener disposed in a substantially linear configuration within an inner passageway of the cannula. A surgical method is provided that includes positioning a distal end of the cannula at a first position relative to a tissue overlying a bone, and advancing a first terminal end of the fastener longitudinally through the inner passageway after the positioning to pass the first terminal end of the fastener out of the inner passageway, through the tissue, and into the bone. After advancing the first terminal end, the distal end of the cannula can be moved from the first position to a second position relative to the tissue, thereby causing the fastener to move from the substantially linear configuration to a bent configuration. After moving the distal end of the cannula, a second terminal end of the fastener can be advanced longitudinally through the inner passageway of the cannula to pass the second terminal end of the fastener out of the inner passageway, through the tissue, and into the bone.

Moving the distal end of the cannula laterally can cause an intermediate portion of the fastener extending between the first and second terminal ends of the fastener to extend through an opening formed in a sidewall of the cannula, and/or can cause the intermediate portion to move from a substantially longitudinal orientation to a substantially lateral orientation.

The fastener can have a variety of configurations. The fastener can be formed from a shape memory material such that the fastener is biased to move from the substantially linear configuration to the bent configuration when the distal end of the cannula is moved from the first position to the second position. In some embodiments, the fastener in the bent configuration can have a width that is greater than a diameter of the inner passageway of the cannula.

In another aspect, a surgical system is provided that includes a surgical fastener having a first leg, a second leg, and an intermediate portion extending therebetween. At least a portion of the surgical fastener is formed from a shape memory material. The surgical fastener is movable between a substantially linear configuration and a default, bent configuration. The first and second legs are configured to be advanced through tissue and into bone with the intermediate portion being positioned outside the bone.

The system can also include a cannula having an inner lumen extending therethrough and having an opening formed through a sidewall thereof at a distal end of the elongate cannula. The opening can extend proximally from a distal-most end of the cannula and terminate distal to a proximal end of the cannula. The surgical fastener can be configured to be disposed within the inner lumen of the cannula in the substantially linear configuration and to move from the substantially linear configuration within the inner lumen to the bent configuration with the first leg advanced out of the inner lumen through the distal-most end of the cannula, the intermediate portion extending through the opening, and the second leg being disposed within the inner lumen. The system can also include a pusher configured to slidably move within the inner lumen of the cannula and push the surgical fastener disposed within the inner lumen to move the surgical fastener to the bent configuration with the first leg advanced out of the inner lumen through the distal-most end of the cannula, the intermediate portion extending through the opening, and the second leg being disposed within the inner lumen.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings.

Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary surgical fasteners and methods and devices are provided for deploying a surgical fastener. In general, the methods and devices allow a surgical fastener to be deployed to secure tissue to bone. In one embodiment, a surgical fastener can be configured to move between a linear or compressed configuration, in which the fastener can have a first maximum width, and a second bent or expanded configuration, in which the fastener can have a second maximum width greater than the first maximum width. The fastener can therefore be configured to be delivered in the compressed configuration into a patient's body through a relatively small opening and move to the expanded configuration within the patient's body to have a larger size in which it can more effectively secure tissue to bone. Generally, in the compressed configuration, the fastener can be substantially straight, and in the expanded configuration, the fastener can be bent, e.g., U-shaped. The fastener can be biased to the expanded configuration such that a force is required to be applied to the fastener to maintain the fastener in the compressed configuration. A delivery device can be configured to advance the fastener through tissue and into bone to attach the tissue to the bone. The delivery device can be configured to apply the force to the fastener to maintain the fastener in the compressed configuration such that when the fastener is released from the delivery device, the fastener can be configured to self-expand from the compressed configuration to the expanded configuration.

In use, as discussed further below, the delivery device can be advanced into a patient's body such that a distal end of the delivery device can be positioned adjacent to tissue to be attached to bone. The surgical fastener in a first straight configuration can be distally advanced through an inner passageway of the delivery device to deploy a first portion of the fastener from the inner passageway and through the tissue and into the bone. The distal end of the delivery device can then be repositioned relative to the tissue and the bone with a second portion of the fastener disposed within the inner passageway of the delivery device, which can allow the fastener to automatically move from the compressed configuration to the expanded configuration. More particularly, repositioning the distal end of the delivery device can cause a third portion of the fastener connecting the first and second portions to extend transverse to the first portion, and optionally to extend through a window formed in the delivery device. With the delivery device at the repositioned location, the second portion of the fastener can be deployed from the inner passageway and through the tissue and into the bone. Delivering a fastener in such a way can allow for the use of very small sized delivery devices, which can be delivered through a very small incision, while still allowing a fastener larger than the very small incision to be deployed in a patient's body and allowing a fastener of adequate size and strength to attach tissue to bone.

The surgical fasteners disclosed herein can be formed from any one or more materials, preferably a biocompatible material(s) safe for use in the body. In an exemplary embodiment, at least a portion of the surgical fastener, e.g., an intermediate portion thereof, can be formed from one or more flexible materials such that the surgical fastener has some degree of elasticity, e.g., can bend without breaking In an exemplary embodiment, the surgical fastener can be formed at least partially from a shape memory material, which can include a single material or a combination of materials. However, the surgical fastener can be made from any type of material and any combination of materials able to provide structure to the implant as discussed below and as appropriate for use in a body. Non-limiting examples of shape memory materials include copper-zinc-aluminum-nickel alloys, copper-aluminum-nickel alloys, nickel-titanium alloys such as Nitinol, thermoplastic materials such as Nylon or Nylon blends, and shape memory polymers such as Veriflex™. The shape memory material can facilitate the surgical fastener being naturally biased to a linear or expanded configuration in which it can be positioned in tissue, as discussed further below. The shape memory material can also facilitate delivery of the surgical fastener into tissue and bone by allowing any or all portions of the surgical fastener to be deformed or bent into a compressed configuration in which the surgical fastener has a relatively small diameter to facilitate delivery of the surgical fastener to tissue and bone while also allowing the surgical fastener to automatically move from the compressed configuration to the surgical fastener's "memorized" shape, in which it has a larger diameter, for implantation within the tissue and bone. In an exemplary embodiment, the entire surgical fastener can be formed from one or more shape memory materials. In another exemplary embodiment, bone-penetrating portions of the surgical fastener can be formed from one or more non-shape memory materials, e.g., titanium, stainless steel, etc., and another portion of the surgical fastener, e.g., an intermediate portion from which the bone-penetrating portions extend, can be formed from one or more shape memory materials. In yet another exemplary embodiment, joints between bone-penetrating portions of the surgical fastener can be formed from one or more shape memory materials, and a remaining portion of the surgical fastener, e.g., the bone-penetrating portions and an intermediate portion from which the bone-penetrating portions extend, can be formed from one or more non-shape memory materials.

The delivery devices disclosed herein can also be formed from any one or more materials, preferably a biocompatible material(s) safe for use in the body. In an exemplary embodiment, at least a portion of the delivery device, e.g., a cannulated portion through which a surgical fastener advances, can be formed from one or more substantially rigid materials, e.g., titanium, stainless steel, etc.

Figure 1:
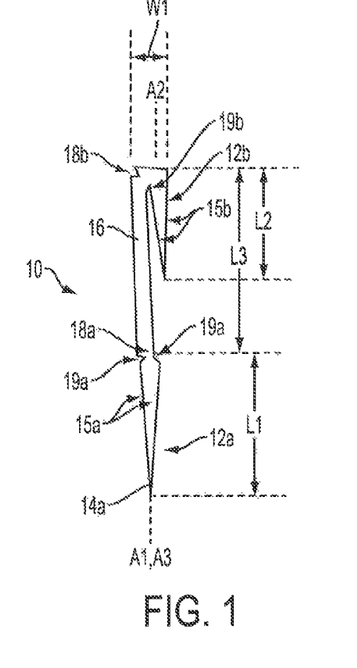
FIG. 1 is a side view of one embodiment of a surgical fastener in a linear configuration.
Figure 2:
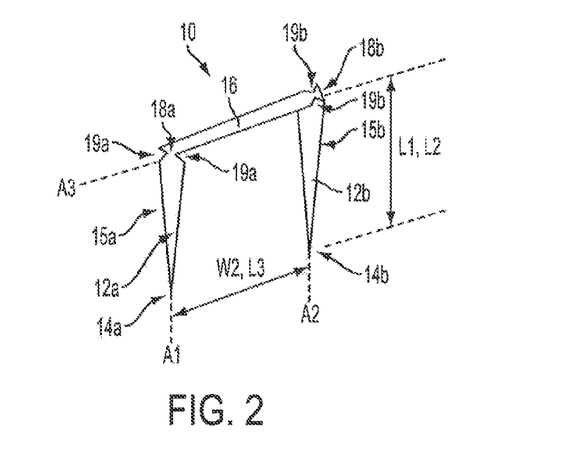
FIG. 2 is a perspective view of the surgical fastener of FIG. 1 in a bent configuration.

In one exemplary embodiment shown in FIGS. 1 and 2, a surgical fastener 10 is provided that can be configured to attach tissue to bone. The fastener 10 can have a variety of sizes, shapes, and configurations. The fastener 10 can include a first leg 12a, a second leg 12b, and a backspan or intermediate portion 16 extending between the first and second legs 12a, 12b. The fastener 10 can also include first and second joints 18a, 18b where the first leg 12a and the second leg 12b respectively couple to the backspan 16. As discussed further below, the first and second legs 12a, 12b can be configured to bend at their respective joints 18a, 18b relative to the backspan 16 to move the fastener between compressed and expanded configurations. The first leg 12a, the second leg 12b, and the backspan 16 are all formed of a same shape memory material(s) in the fastener 10 of FIGS. 1 and 2, but, as mentioned above, a fastener can be formed of a variety of one or more materials in various portions thereof The fastener 10 can be configured to move between a compressed or linear configuration, shown in FIG. 1, and an expanded or bent configuration, shown in FIG. 2. The fastener 10 can be biased to the expanded configuration, which can facilitate deployment of the fastener 10 into tissue, as discussed further below. The fastener 10 can be biased to the expanded configuration, such as by being at least partially formed of a shape memory material "memorized" to the expanded configuration. The fastener 10 can therefore be configured to naturally be in the expanded configuration and to be in the compressed configuration when an external force is applied thereto, such as by the fastener 10 being compressed by hand and/or being positioned within a cannula, as discussed further below. For clarity of illustration, FIG. 1 omits the external force. Because the fastener 10 can be formed at least partially from a shape memory material(s), the legs 12a, 12b can be configured to automatically move between the expanded and compressed configurations, e.g., depending on whether the external force is being applied to the fastener 10 or not. In an exemplary embodiment, at least the first and second joints 18a, 18b can be formed from of a shape memory material(s) to facilitate movement of the legs 12a, 12b relative to the backspan 16.

In the compressed or linear configuration, the fastener 10 can be substantially straight. When the fastener 10 is in the compressed configuration, a first longitudinal axis A1 of the first leg 12a is substantially parallel to a second longitudinal axis A2 of the second leg 12b and the first longitudinal axis A1 of the first leg 12a is substantially coaxial with a third longitudinal axis A3 of the intermediate portion 16. Also, in the straight configuration the second longitudinal axis A2 of the second leg 12b is substantially parallel to the third longitudinal axis A3 of the intermediate portion 16 and second leg 12b is adjacent to and can be in contact with intermediate portion 16. The fastener 10 in the compressed configuration can have a first maximum width W1 and a first maximum height H1. The first maximum width W1 can vary, but in an exemplary embodiment the first maximum width W1 can be less than about 5 mm, e.g., less than about 2 mm, e.g., about 1.5 mm. Penetrating distal tips 14a, 14b of the legs 12a, 12b can each be directed or point in a same direction, e.g., distally, when the fastener 10 is in the compressed configuration, which can facilitate deployment of the legs 12a, 12b into tissue and/or bone, as discussed further below.

In the expanded configuration, the fastener 10 can be non-straight and can have a U-shape. The U-shape can allow the fastener 10 to have a symmetrical shape when the fastener 10 is in the expanded configuration, as shown in FIG. 2. Thus, when the fastener 10 is in the expanded configuration, the first longitudinal axis A1 of the first leg 12a and the second longitudinal axis A2 of the second leg 12b can be substantially parallel to one another, and the third longitudinal axis A3 of the intermediate portion 16 can be angularly offset from or non-parallel with the first and second longitudinal axes A1, A2. Such substantially parallel axes can facilitate disposal of the fastener 10 in and advancement of the fastener 10 through a delivery device, as discussed further below. As in the illustrated embodiment, the third longitudinal axis A3 of the intermediate portion 16 can be substantially perpendicular to the first and second longitudinal axes A1, A2 when the fastener 10 is in the expanded configuration. In another embodiment, a fastener can have a U-shape, but an intermediate portion of the fastener can have an arcuate shape when the fastener is in the expanded configuration such that a third longitudinal axis of the intermediate portion of the fastener can be offset from longitudinal axes of first and second legs of the fastener at a non-perpendicular angle.

The fastener 10 in the expanded configuration can have a second maximum width W2 greater than the first maximum width W1, and can have and a second maximum height H2 less than the first maximum height H1. The second maximum width W2 can generally be defined by a longitudinal length L3 of the intermediate portion 16, and the second maximum height can generally be defined by longitudinal lengths L1, L2 of the first and second legs 12a, 12b. The second maximum width W2 can vary, but in an exemplary embodiment the second maximum width W2 can be greater than about 5 mm, e.g., greater than about 8 mm, e.g., about 10 mm. In other words, the second maximum width W2 can be at least four times the first maximum width W1, which can allow the fastener 10 to be delivered through a lumen having a diameter about four times smaller than the width W2 of the fastener 10 in the expanded configuration. The first and second legs 12a, 12b have substantially the same longitudinal lengths L1, L2 in the illustrated embodiment, but one of the legs 12a, 12b can have a longer longitudinal length than the other. In such a case the longer of the legs can define the fastener's maximum height in the expanded configuration. The longitudinal lengths L1, L2 of the first and second legs 12a, 12b of the fastener 10 can vary relative to the longitudinal length L3 of the intermediate portion 16. For example, the legs 12a, 12b can each have a longitudinal length that is greater than, substantially equal to, or less than the longitudinal length of the intermediate portion 16. In an exemplary embodiment, the legs 12a, 12b can have longitudinal lengths L1, L2 that are each greater than the longitudinal length L3 of the intermediate portion 16, which can allow the fastener 10 to be deployed into tissue having a thickness greater than a desired span of the tissue to be attached with the fastener 10 across which the intermediate portion 16 extends and/or abuts. In another exemplary embodiment, the legs 12a, 12b can have longitudinal lengths L1, L2 that are each less than the longitudinal length L3 of the intermediate portion 16.

Figure 3:
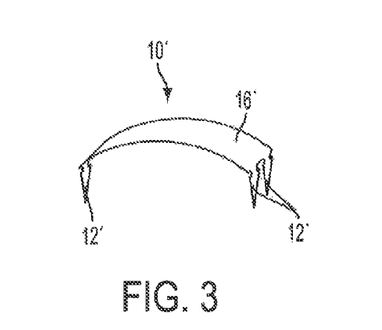
FIG. 3 is perspective view of another embodiment of a surgical fastener in a bent configuration.
Figure 4:
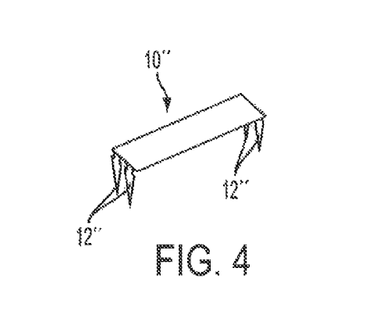
FIG. 4 is perspective view of yet another embodiment of a surgical fastener in a bent configuration.

The first and second legs 12a, 12b can each have a variety of sizes, shapes, and configurations. In an exemplary embodiment, the first and second legs 12a, 12b are identical to one another, as shown in FIGS. 1 and 2. In another embodiment, a surgical fastener can include two different legs, e.g., legs having different lengths and/or widths, which can allow a surgical fastener to be selected for use in accordance with particular tissue and bone to which the fastener is to be attached. For non-limiting example, a tissue can have different thicknesses in different portions thereof such that a fastener including two bone legs of different lengths can be selected such that a first, shorter leg can be advanced through a thinner portion of the tissue, and a second, longer leg can be advanced through a thicker portion of the tissue, thereby allowing the fastener to better approximate a size of the tissue than a fastener having legs of a same length. Additionally, although the fastener 10 of FIGS. 1 and 2 includes two legs 12a, 12b, any fastener can include any number of legs. FIG. 3 illustrates an exemplary embodiment of a fastener 10' including three legs 12', and FIG. 4 illustrates an exemplary embodiment of a fastener 10" including three legs 12". The fastener 10' of FIG. 3 and the fastener 10" of FIG. 4 and their various elements can be generally configured and used similar to other like-named elements discussed herein.

Referring again to FIGS. 1 and 2, the first and second legs 12a, 12b are integrally formed with the backspan 16 in the illustrated embodiment. Having an integral fastener can ease manufacturing of the fastener. However, in another embodiment, one or more legs of a surgical fastener can be removably and replaceably coupled to a backspan or intermediate portion of the fastener, which can allow legs to be selected for use in accordance with particular tissue and bone to which the fastener is to be attached. The leg(s) can be removably and replaceably coupled to the backspan or intermediate portion of the fastener in a variety of ways, e.g., threaded connection, snap fit, compression fit, etc.

Figure 5:
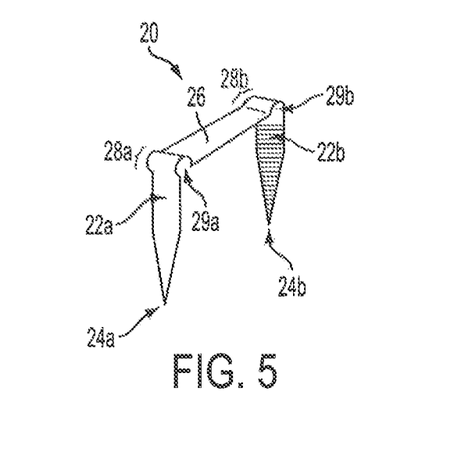
FIG. 5 is a perspective view of another embodiment of a surgical fastener in a bent configuration.

The first and second legs 12a, 12b can each be configured as penetrating members or burrs configured to penetrate tissue and bone. The first and second legs 12a, 12b can therefore include the penetrating distal tip 14a, 14b configured to facilitate penetration of the legs 12a, 12b through tissue and bone. The penetrating distal tips 14a, 14b can each be pointed and sharp as shown in FIGS. 1 and 2, or the penetrating tips can each be blunt. A fastener's penetrating tips can be different from one another. The penetrating distal tips 14a, 14b can also each taper toward respective terminal ends thereof, which can further facilitate penetration of the first leg 12a and second leg 12b through tissue and into bone. In other words, the first leg 12a and the second leg 12b can each have a triangle shape. As will be appreciated by a person skilled in the art, the first leg 12a and second leg 12b can have a number of other shapes. Although the first and second legs 12a, 12b are substantially planar or two-dimensional in the illustrated embodiment, a fastener can include leg(s) that are three-dimensional, e.g., cone-shaped legs. FIG. 5 illustrates an exemplary embodiment of a fastener 20 having first and second substantially planar or two-dimensional legs 22a, 22b extending from opposite ends of a backspan 26, each of the legs 22a, 22b having a substantially rectangular shape in a proximal portion thereof and a substantially triangular shape in a distal portion thereof. A length of the proximal portion relative to a length of the triangular distal portion can vary.

Referring again to the embodiment of FIGS. 1 and 2, one or both of the first and second legs 12a, 12b can include one or more penetration features configured to facilitate penetration of the first leg 12a and the second leg 12b through tissue and bone. In this way, advancing the legs 12a, 12b can require less force, which can ease implantation of the fastener within a body. In the illustrated embodiment, first and second edges 15a, 15b of, respectively, which define the shapes of the legs 12a, 12b, can be sharpened along entire or partial lengths thereof. Another non-limiting example of a penetration feature includes a polymer or other smooth coating along entire or partial surface areas of the legs 12a, 12b.

One or both of the first and second legs 12a, 12b can include one or more retention features configured to aid in retention of tissue to the fastener 10 and/or to hinder removal of the legs 12a, 12b from tissue and/or bone into which they have penetrated. The one or more retention features can therefore help prevent the legs 12a, 12b from slipping or dislodging from tissue and/or bone, which can facilitate healing. As one non-limiting example of a retention feature, the fastener 10 can include first and second cut-outs 19a, 19b. The first and second cut-outs 19a, 19b can be located at the first and second joints 18a, 18b where the first leg 12a and the second leg 12b respectively attach to the backspan 16, which can encourage bending of the legs 12a, 12b relative to the backspan 16 at the joints 18a, 18b as discussed further below, in addition to aiding in tissue retention by allowing tissue to be received therein. Although, the fastener can include retention feature(s) anywhere therein, e.g., in the legs and/or backspan. Each of the legs 12a, 12b include two opposed cut-outs 18a, 18b, although the legs 12a, 12b can include any number of cut-outs and any number of retention features. The cut-outs 19a, 19b can each have a triangular shape, as shown, or can have any other shape, e.g., semi-circle, rectangular, etc., same or different from any other cut-outs formed in the fastener. Other non-limiting examples of retention features include one or more protrusions, e.g., barbs, teeth, etc. extending from the edges 15a, 15b and/or other portion of the legs 12a, 12b, a textured surface, a jagged edge, a zig-zag edge, a sticky coating, etc. The one or more protrusions can be directed to point toward the joints 18a, 18b so as to be configured to substantially not provide resistance to pushing of the legs 12a, 12b down through tissue and/or bone while being configured to resist pulling of the legs 12a, 12b up through tissue and/or bone. Additionally or alternatively, the intermediate portion 16 can include at least one retention feature at least on an interior surface thereof, which can help retain the intermediate portion 16 in a substantially fixed position relative to tissue in which the fastener 10 is deployed.

By being located at the first and second joints 18a, 18b, the first and second cut-outs 19a, 19b can not only be configured to aid in retaining tissue, e.g., by seating tissue therein as discussed further below, the first and second cut-outs 19a, 19b can be configured to aid in pivoting of the first leg 12a and the second leg 12b relative to the backspan 16 by defining a pivot point at which the fastener 10 can be biased to bend or pivot, e.g. define locations of the joints 18a, 18b. Although the pivot points at the joints 18a, 18b in the illustrated embodiment are defined by the cut-outs 19a, 19b, a fastener can include additional or alternative elements defining pivot points, e.g., a thinned area of material, one or more score lines, a hinge, etc.

The fastener 20 of FIG. 5 includes a first retention feature in the form of a textured surface formed on interior surfaces of each of the legs 22a, 22b, and a second retention feature in the form of first and second interior channels 29a, 29b. The textured surface can have a variety of configurations. For non-limiting example, the textured surface can be a series of substantially parallel lines formed from either depressions or raised surfaces on the interior surfaces of the first leg 22a and the second leg 22b. The parallel lines can be at any angle relative to longitudinal axes of their respective first leg 22a and second leg 22b. For another non-limiting example, the textured surface can have a randomized textured surface. Although the textured surface is only on interior surfaces of the first and second legs 22a, 22b, the textured surface can be on any one or more portions of the first leg 22a and the second leg 22b.

The first and second interior channels 29a, 29b can have a variety of sizes, shapes, and configurations. The first and second interior channels 29a, 29b can be respectively defined by first and second joints 28a, 28b at which the first and second legs 22a, 22b respectively coupled to the backspan 26. The first and second interior channels 29a, 29b can be defined by interior surfaces of their respective joints 28a, 28b, although the interior channels 29a, 29b can have other shapes. The size and shape of the first and second interior channels 29a, 29b can therefore be defined by interior surfaces of their respective joints 28a, 28b, which in the illustrated embodiment have c-shaped cross-sections. When the fastener 20 is delivered through tissue and into bone, a volume of tissue can be anchored or trapped within the arc shaped interior channels 29a, 29b, which can improve the retention of tissue to the fastener 20. The size and shape of the interior channels 29a, 29b can affect the volume of tissue captured by the retainer and the bending characteristics of the joints 28a, 28b.

Referring again to the embodiment of FIGS. 1 and 2, the backspan 16 can have any size, shape, and configuration. In the illustrated embodiment, the backspan 16 has a substantially rectangular shape, although the backspan 16 can have other shapes, e.g., diamond-shaped, ovular, zig-zag, arcuate, a Y shape with three legs extending therefrom, an X shape with four legs extending therefrom, etc. FIG. 3 illustrates an example of an arcuate backspan 16'. While in the illustrated embodiment of FIGS. 1 and 2 the backspan 16 is substantially planar and linear, the backspan 16 can have any number of other forms, such as in the form an arc at least when the fastener is in the expanded configuration, which can facilitate retention of a larger volume of tissue than a planar backspan.

Various deployment devices can be used to deploy a surgical fastener in tissue and bone. In general, a deployment device configured to deliver any of the surgical fasteners discussed herein into a body of a patient can have a passageway extending therethrough that can be sized to allow at least one fastener to be advanced therethrough. Generally, the deployment device can be configured to be inserted through an opening in a patient's body, e.g., an incision formed in a patient, to position a proximal end of the deployment device outside the patient and a distal end of the deployment device within the patient at a first location. With the distal end of the deployment device positioned at the first location within the patient, the distal end of the deployment device can be positioned adjacent a tissue, and a fastener can be advanced through the passageway of the deployment device and into the tissue and into bone underlying the tissue. The deployment device can be configured to be repositioned relative to the tissue and the bone after a first portion of the fastener, e.g., one leg thereof, is deployed into the tissue and the bone, with a second portion of the fastener, a second leg thereof remaining disposed within the deployment device. The second portion of the fastener can then be deployed from the deployment device at a second location a distance away from the first location, thereby allowing a backspan of the fastener to extend between the first location and the second location. The deployment device can be configured to have one or more fasteners positioned with the passageway thereof when the deployment device is inserted into the patient, although in some embodiments, one or more fasteners can be positioned within the passageway of a delivery device after the delivery device is inserted into a patient.

Figure 6:
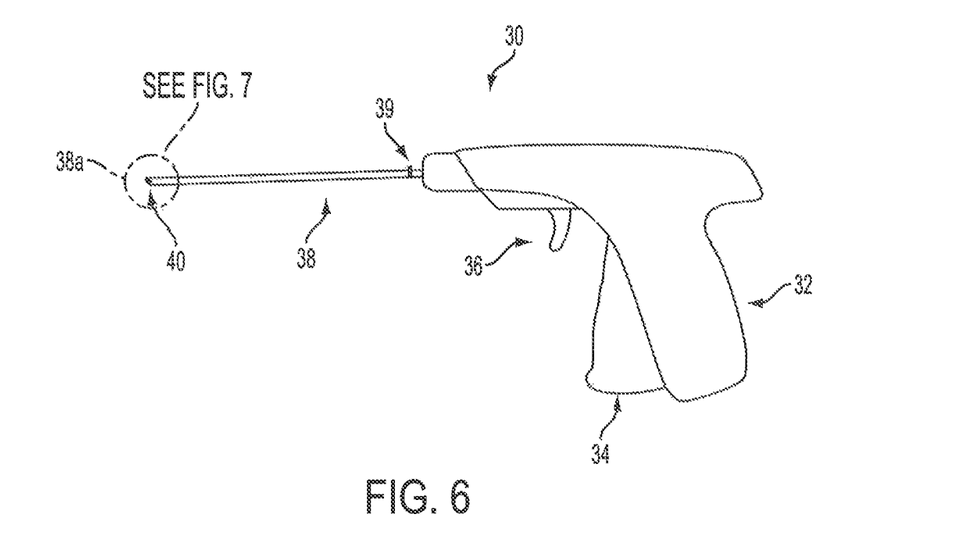
FIG. 6 is a side view of one embodiment of a surgical fastener delivery device.
Figure 7:
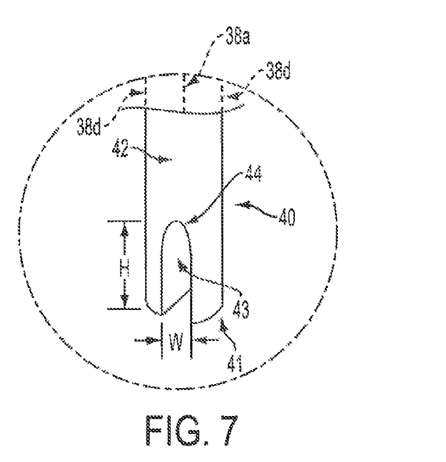
FIG. 7 is a perspective view of a distal end of the surgical fastener delivery device of FIG. 6.

FIGS. 6 and 7 illustrate an exemplary embodiment of a deployment device 30 configured to deliver any one or more of the fasteners discussed herein to tissue and bone. The device 30 can include a cannulated elongate body 38 having a passageway 41 extending therethrough. The passageway 41 can be configured to have at least one fastener (not shown) received therein. The at least one fastener can be pre-loaded in the passageway 41, or the fastener(s) can be manually positioned therein prior to use of the fastener(s). The elongate body 38 is shown as a cannulated elongate body of a device 30 having a handle 32 from which the elongate body extends distally, but a delivery device can include a standalone cannulated member having open proximal and distal ends.

The handle 32 can have a variety of sizes, shapes, and configurations. In the illustrated embodiment, the handle 32 includes a first actuator, e.g., a first trigger 34, and a second actuator, e.g., a second trigger 36. The triggers 34, 36 can be located anywhere on the handle 32. The handle 32 can be configured to allow a user to hold and operate the deployment device 30 with a single hand. The delivery device 30 can include a magazine (not shown) configured to contain one or more fasteners therein and to be loaded within the device 30 for deployment of the fastener(s) from the magazine. The first trigger 34 can be configured to be actuated, e.g., manually depressed, to advance a first fastener (not shown) distally through the passageway 41 of the cannula 38 out of a distal end 40 of the cannula 38. The second trigger 36 can be configured to be actuated, e.g., manually depressed, to advance a second fastener (not shown) distally through the passageway 41 of the cannula 38 and out of the distal end 40 of the cannula 38. As discussed further below, the deployment device 30 can be configured to deliver multiple fasteners to a surgical site within a body of a patient without the need to remove the distal end 40 of the cannula 38 from the patient. Although the device 30 includes two triggers, a deployment device can have a single trigger configured to be actuated to deploy one or more fasteners from the cannula 18. Also, the deployment device can have one or more actuators other than one or more triggers configured to advance one or more fasteners through a passageway of a cannula of the device, e.g., e.g., a rotatable knob, a lever, a push button, etc. The handle 32 can also include an actuator (not shown), e.g., a rotatable knob, a lever, a push button, etc., configured to rotate the cannula 38 about a longitudinal axis 38A thereof relative to the handle 32, which can help facilitate positioning of the fastener(s) relative to tissue in which the fastener(s) are deployed, as discussed further below.

The cannula 38 can have any size, configuration, and shape. The cannula 38 can have a cylindrical shape with a circular cross section, although the cannula 38 can have any other shape capable of delivering a surgical fastener. The cannula 38 can have any diameter. In one embodiment, the cannula 38 can have an external diameter 38D of a size to allow insertion thereof through an opening, e.g., an incision, formed in a patient's skin such that the distal end 40 of the cannula 38 can be positioned adjacent to tissue overlying bone. By way of a non-limiting example, the external diameter 38D of the cannula 38 can be sized for minimally invasive surgery, e.g., have a diameter in a range of about 1.5 to 10 mm. In an exemplary embodiment, the external diameter 38D can be constant along a longitudinal length thereof, but the external diameter can vary, e.g., be greater at a proximal end of the cannula 38 than at the distal end 40.

An internal diameter (not shown) of the cannula 38, e.g., a diameter of the passageway 41, can also vary, and can be sized to allow disposal of a fastener(s) therein, and advancement of the fastener(s) therethrough. The passageway 41 can therefore be configured to provide a force to the fastener(s) to hold the fastener(s) in a compressed configuration. The cannula 38 can be configured to have the fastener(s) disposed therein individually or as part of a magazine or cartridge having a plurality of fasteners loaded therein. In an exemplary embodiment, a cartridge can include two fasteners. The cannula 38 can be configured to have one or more magazines or cartridges loaded therein.

The cannula 38 can have any longitudinal length, including a shorter longitudinal length where a user of the device 30 can manipulate the deployment device 30 close to a patient, or a longer longitudinal length, where the surgeon can manipulate the deployment device 30 more remotely from the patient. In an exemplary embodiment, the cannula 38 can be rigid along its longitudinal length, which can facilitate holding the fastener(s) disposed in the passageway 41 thereof in a compressed configuration. However, one or more portions of the cannula 38 can be flexible. For non-limiting example, a proximal portion of a cannula in which fastener(s) are not disposed can be flexible, while a distal portion of the cannula in which the fastener(s) are disposed can be rigid.

As shown in FIG. 7, the distal end 40 of the cannula 38 can have an opening or window 43 formed through a sidewall 42 thereof. In an exemplary embodiment, the cannula 38 can have a single opening 43 formed therethrough, which can provide predictability of where a fastener can be advanced therethrough, as discussed further below. Generally, the opening 43 can be configured to allow an intermediate portion of a fastener (not shown) to pass therethrough such that a first portion of the fastener, e.g., a first leg, can be positioned within the cannula 38, e.g., within the inner passageway 41 of the cannula 41, and a second portion of the fastener, e.g., a second leg, can extend through the opening 43 to position a third portion of the fastener, e.g., a backspan, at least partially external to the cannula 38.

The opening 43 can have a variety of sizes and shapes. Generally, the opening 43 can have a size and shape configured to allow an intermediate portion of a fastener to extend therethrough. In an exemplary embodiment, the opening 43 can have a U-shape and can extend proximally from a distal-most end of the cannula 38 and terminate distal to a proximal end (not shown) of the cannula 38. However, the opening 43 can have other shapes, e.g., rectangular, circular, triangular etc. The opening 43 can have any width W and any height H. In an exemplary embodiment, the width W can be less than half a perimeter or circumference of the cannula 38 at the distal end 40 thereof. In other words, the width W can be less than the outer diameter 38D of the cannula 38, at least at the distal end 40 thereof. The width W can be constant along the height of the opening 38, or the width W can vary therealong, e.g., be narrower at a proximal end thereof than at a distal end thereof to facilitate guidance of a fastener(s) therethrough. The width W can be greater than a maximum width of an intermediate portion or backspan of a fastener to be advanced therethrough, thereby allowing free passage of the fastener's intermediate portion or backspan therethrough.

In an exemplary embodiment, the opening 43 can have a height H that allows a fastener(s) to extend therethrough. Although the height H of the opening 43 can be greater than a longitudinal length of a fastener disposed in a compressed configuration within the inner passageway 41 of the cannula 38, in an exemplary embodiment, the height H of the opening 43 can be less than the longitudinal length of a fastener disposed in a compressed configuration within the inner passageway 41 of the cannula 38, which can help prevent the fastener from prematurely advancing through the opening 43. In an exemplary embodiment, the height H of the opening 43 can be less than the greater of a maximum longitudinal length of a bone-penetrating portion of the fastener and a maximum longitudinal length of an intermediate portion or backspan of the fastener, which can help prevent the fastener from extending through the opening 43 until the bone-penetrating portion at least partially penetrates into tissue and/or bone. The height H can be selected such that an intermediate portion of a fastener disposed within the cannula 38 and being deployed therefrom can contact a proximal end 44 of the opening 43 during the fastener's advancement through the opening 43, which can facilitate movement of the fastener from a substantially straight configuration to a bent configuration.

The cannula 38 can include one or more alignment mechanisms configured to indicate a location of the opening 43. In other words, the one or more alignments mechanisms can indicate a radial position of the opening 43 around the perimeter or circumference of the cannula 38. In this way, when the distal end 40 of the cannula 38 is disposed within a body of a patient, the one or more alignment mechanisms can visually indicate from outside the body a location of the opening 43. Knowing the location of the opening 43 can facilitate deployment of one or more fasteners disposed within the cannula 38, as discussed further below. The one or more alignment mechanisms can have a variety of sizes, shapes, and configurations. In an exemplary embodiment, one or more alignments marks can be formed on a proximal end of the cannula 39 adjacent to and outside the handle 32. Thus, if the cannula 38 is configured to rotate relative to the handle 32, or if the cannula 38 is removably and replaceably matable to the handle 32, the one or more alignment marks can remain in proper alignment with the opening 43. In one embodiment, the one or more alignment marks can include a numeric, alphabetic, and/or other symbol, e.g., an "X," a dot, etc., printed, embossed, or otherwise visually present on the proximal end of the cannula 38. In another embodiment, the one or more alignment marks can include a longitudinally extending mark, e.g., at least one line, etc., printed, embossed, or otherwise visually present on the cannula 38.

Figure 8:
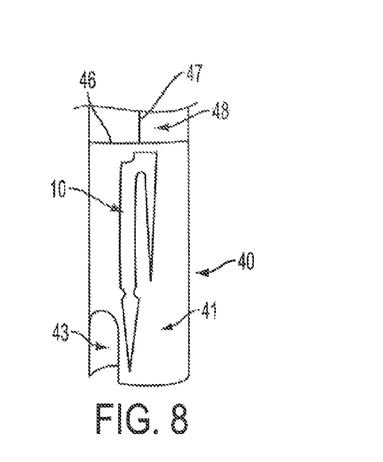
FIG. 8 is a perspective, partially transparent view of the surgical fastener of FIG. 1 and a pusher disposed within the distal end of the surgical fastener delivery device cannula of FIG. 7.

The delivery device 30 can also include a pusher 48, shown in FIG. 8, configured to be slidably movable through the passageway 41 of the cannula 38, e.g., longitudinally movable along the longitudinal axis 38A of the cannula 38, to push at least one fastener positioned in the passageway 41 distally therethrough and into tissue and bone underlying the tissue. The pusher 48 can have a variety of sizes, shapes, and configurations. The distal end 46 of the pusher 48 can have an enlarged diameter, e.g., be configured as a ball, a cone, a pyramid, a block, etc., compared to an elongate shaft 47 of the pusher 48. The enlarged diameter can facilitate contact of the pusher 48 with one or more fasteners while facilitating advancement of the shaft 47 through the passageway 41 of the cannula 38. The distal end 46 of the pusher 48 can have a size and shape corresponding to a size and shape of the passageway 41 of the cannula 38, e.g., have a circular disc shape corresponding to a cylindrical passageway and a diameter less than a diameter of the passageway. In an exemplary embodiment, the distal end 46 of the pusher 48 can include a concavity that can centrally locate and contact a fastener disposed within the inner passageway 41 and guide the fastener within the inner passageway 41.

In an exemplary embodiment, the pusher 48 can be rigid along its longitudinal length, which can facilitate advancing the fastener(s) through the passageway 41 of the cannula 38. However, one or more portions of the pusher 48 can be flexible. For non-limiting example, a proximal portion of a pusher can be flexible, while a distal portion of the pusher including the distal end thereof can be rigid.

The distal end 46 of the pusher 48 can include at least one mating feature (not shown) configured to operatively connect with the fastener 10 such that rotation of the pusher 48, e.g., about a longitudinal axis of the shaft 48, can cause a corresponding rotation of the fastener 10. The at least one mating feature can have various sizes, shapes, and configurations. In one embodiment, the at least one mating feature can include at least one distally-extending protrusion configured to releasably engage a proximal end of a fastener. If a delivery device includes one or more fastener cartridges, the at least one mating feature of the device's pusher can be configured to operatively connect with the fastener cartridge, similar to that discussed above. The at least one mating feature can optionally be configured to allow the cartridge to be pulled proximally through the device's cannula when the pusher is pulled proximally, which can allow removal of the cartridge from the cannula and/or allow repositioning of the cartridge relative to an opening formed through the cannula.

The pusher 48 can include one or more alignment marks (not shown) configured to include a relative position of the pusher relative to the cannula 38 when the pusher 48 is disposed within the passageway 41 of the cannula 38. The one or more alignment marks can have a variety of configurations, e.g., a numeric mark, an alphanumeric mark, a symbol, a line, a circumferential ring, etc. at one or more location along a longitudinal length of the pusher 48, e.g., in a proximal portion of the shaft 47. In this way, a user can observe the one or more alignment marks relative to the cannula 38 to help avoid under-insertion and/or over-insertion of a fastener into tissue and/or bone by monitoring the position of the one or more alignment marks relative to a proximal portion of delivery device 30.

In some embodiments, a delivery device can include multiple pushers that can be configured to be slidably movable relative to one another within an inner passageway of a cannula. In an exemplary embodiment, each of the pushers can be configured to advance one of a plurality of fasteners disposed within the inner passageway. The device can include one actuator configured to actuate each of the pushers, e.g., actuate the pushers in a sequential order, or the device can include a dedicated actuator for each of the pushers.

As mentioned above, in an exemplary embodiment, one or more fasteners can be pre-loaded into the passageway 41, but the one or more fasteners can be loaded in the passageway 41 after the pusher 48 is inserted into the passageway 41, e.g., by being advanced through the distal end 40 of the cannula 38. A proximal end (not shown) of the device 30 can include an actuator, e.g., the first trigger 34 and/or the second trigger 36, configured to move the pusher 48 within the passageway 41 of the cannula 38, and a user can engage the actuator to advance the pusher 48 distally through the passageway 41.

In another exemplary embodiment, a delivery device can include an elongate tubular member, e.g., a standalone cannula having open ends. The tubular member can be configured to have a fastener advanced through a proximal end thereof to be disposed within an inner passageway extending through the elongate member. A distal end of a pusher can be configured to be inserted through a proximal end of the tubular member and into a passageway thereof to engage a proximal end of a fastener disposed within the passageway. Particularly if the pusher is a separate element from the elongate tubular member, a proximal end of the pusher can include a handle configured to facilitate handling of the pusher. The pusher can include a pusher alignment mark at a proximal end thereof in addition to or in alternative to an alignment mark(s) formed on the tubular member to help indicate a location of an opening formed in a distal end of the tubular member.

Figure 9:
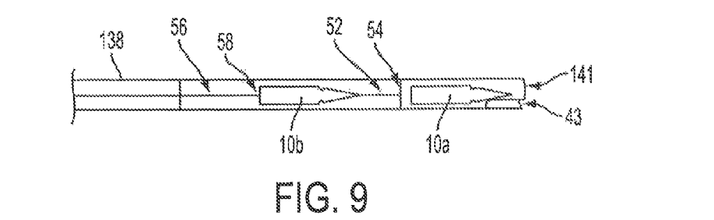
FIG. 9 is a side view of one embodiment of a distal end of a delivery device cannula having two pushers and two fasteners disposed therein.

As mentioned above, a delivery device can be configured to deliver multiple fasteners without requiring removal of the delivery device from the surgical site for reloading of fasteners. One embodiment of such a delivery device is illustrated in FIG. 9. The delivery device includes an elongate tubular member 138 having a first pusher 52 and a second pusher 56 movably disposed in an inner passageway 141 thereof. The first and second pushers 52, 56 can each be configured to advance a fastener 10*a*, 10*b* through the passageway 141 and out a distal end of the tubular member 138. The first pusher 52 and the second pusher 56 can have respective distal ends 54, 58 configured to engage their respective fasteners 10*a*, 10*b*. The first pusher 52 can have a size and shape that allows the first pusher 52 to advance the first fastener 10*a* through the passageway 141 and out of the tubular member 138 to be deployed in tissue and/or bone. The size and shape of the first pusher 52 can also allow the first pusher 52 to be moved proximally through the passageway 141 after deploying the first fastener 10*a* so as to allow the second pusher 56 to be distally advanced within the passageway 141 to advance the second fastener 10 through the passageway 141 and out of the tubular member 138 to be deployed in tissue and/or bone. In one embodiment, a delivery device configured to deliver multiple fasteners can include one or more fastener cartridges (not shown) where each cartridge includes two or more fasteners seated therein. A pusher (not shown) can mate to the cartridge to distally advance the cartridge to the distal end of the tubular member 138, and a member disposed on the distal end of the pusher can advance each fastener from the cartridge and into tissue and/or bone. In another embodiment, a delivery device configured to deliver multiple fasteners, the delivery device can include a single pusher and a magazine of fasteners where the pusher can sequentially advance fasteners from the magazine while the delivery device remains disposed within a patient's body.

Any of the surgical fasteners discussed herein can be provided as part of a kit including a plurality of surgical fasteners each having a different size, shape, and/or configuration. In this way, the surgical fastener(s) having the most appropriate size and strength for use in a particular surgical procedure with a particular patient can be selected for use from the kit. Similarly, any of the delivery devices discussed herein can be provided as part of a kit including a plurality of different delivery devices varying in one or more ways, e.g., cannula length, maximum diameter, flexibility, etc., such that one of the delivery devices can be selected for use from the kit in accordance with a particular surgical procedure and/or a particular patient. The kit including the plurality of different delivery devices can also include a plurality of different surgical fasteners.

The surgical fasteners and delivery devices discussed herein can be used in a variety of surgical procedures in which a surgical fastener can facilitate attachment of tissue to bone, e.g., ACL repair, rotator cuff repair, etc. In an exemplary embodiment, a procedure including passage of a surgical fastener into a patient's body can be a minimally invasive procedure, but as will be appreciated by a person skilled in the art, the surgical fasteners and delivery devices discussed herein also have application in open surgical instrumentation as well as application in robotic-assisted surgery.

FIGS. 10-15 illustrate an exemplary embodiment of a surgical procedure that includes advancing the fastener 10 into a body of a patient. Although this exemplary embodiment is discussed with reference to the fastener 10 shown in FIGS. 1 and 2, and to the delivery device 30 shown in FIGS. 6 and 7, any of the surgical fasteners and any of the delivery devices discussed herein can be advanced into a patient's body in this or other ways.

The surgical procedure can include preparing the patient for surgery using standard techniques. In a minimally invasive procedure, one or more introducer devices (not shown), e.g., a cannula, a trocar, etc., can be advanced through an opening in the patient to provide access to a surgical site. The cannula 38 of the delivery device 30 can be introduced into the patient through such an introducer device, or advanced directly into the patient. A person skilled in the art will appreciate that one or more viewing devices, e.g., a scoping device such as an endoscope, can be advanced into the body through an incision through which the cannula 38 of the delivery device 30 is introduced into the patient, or through another opening, e.g., another incision or a natural orifice, to provide visualization of the surgical site from outside the body.

Figure 10:
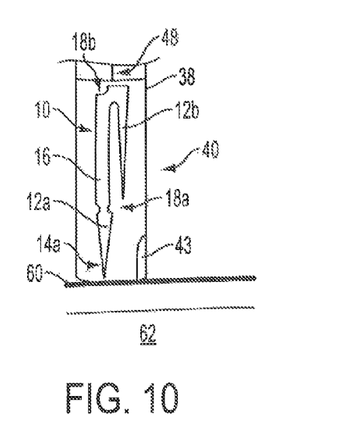
FIG. 10 is a side, partially transparent view of the distal end of the surgical fastener delivery device cannula of FIG. 7 having the pusher of FIG. 8 disposed therein, having the surgical fastener of FIG. 1 disposed therein, being positioned adjacent tissue and bone.

As shown in FIG. 10, the fastener 10 can be positioned in the compressed configuration within the passageway 41 of the delivery device 40 for deployment in a tissue 60 and/or a bone 62. As mentioned above, when the fastener 10 is positioned within the passageway 41 of the cannula 38, distal tips 14*a* and 14*b* are oriented distally and the first and second legs 12*a*, 12*b* and the backspan 16 can each extend longitudinally in a proximal-distal direction relative to the cannula 38 with their respective longitudinal axes A1, A2, A3 being substantially parallel to the longitudinal axis 38A of the cannula 38, as shown in FIG. 10. As also mentioned above, the fastener 10 can be positioned within the passageway 41 in a variety of ways, such as by being advanced into the proximal end of the delivery device 40, e.g., through a hole or opening at a proximal end of the handle 32 in communication with a proximal end of the cannula 38. Such a configuration can allow the first distal tip 14*a* to be a first portion of the fastener 10 advanced into contact with the tissue 60 and with the bone 62 underlying the tissue 60. The fastener 10 can be positioned in passageway 41 in the compressed configuration with the first leg 12a, e.g., the distal tip 14a thereof, leading the fastener 10, e.g., being a distal-most portion of the fastener 10 within the passageway 41. The fastener 10 can therefore be asymmetrically bent in the compressed configuration, e.g., bent at the second joint 18b and unbent at the first joint 18a, as shown in FIG. 10. In another embodiment, a fastener disposed within the passageway 41 can be bent elsewhere along a longitudinal length thereof, e.g., at a point along the longitudinal length L3 of the backspan 16. In an exemplary embodiment, the fastener 10 can be bent or folded at one point thereof, e.g., at the second joint 18b, which can facilitate deployment of the fastener 10 from the cannula 38, as discussed further below. Although only one fastener 10 is shown disposed in the passageway 41 of the cannula 38, as mentioned above, the cannula 38 can be configured to have multiple fasteners simultaneously disposed therein. Additionally, although FIGS. 10-15 illustrate deployment of a single fastener 10, as mentioned above, multiple fasteners can be deployed from a delivery device without the device being removed from the patient's body.

With the fastener 10 loaded in the delivery device 30, the distal end 40 of the cannula 38 can be positioned at a first location adjacent to the tissue 60 and to the bone 62. Alternatively, as mentioned above, the distal end 40 of the cannula 38 can be positioned at the first location adjacent to the tissue 60 prior to the fastener 10 being loaded in the passageway 41.

Figure 11:
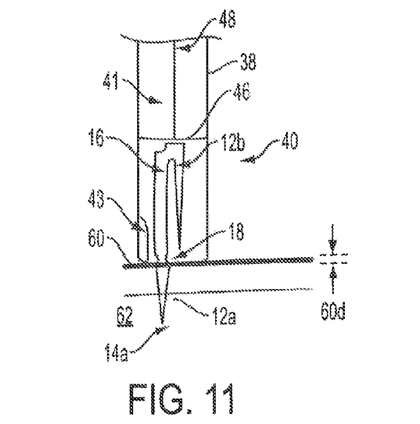
FIG. 11 is a side, partially transparent view of the pusher of FIG. 11 advancing a first leg of the surgical fastener of FIG. 11 out of the distal end of the surgical fastener delivery device cannula of FIG. 11, through the tissue, and into the bone.

As shown in FIG. 11, with the distal end 40 of the cannula 38 positioned at the first location, the first leg 12a of the fastener 10 can be deployed from the cannula 38 to advance through the tissue 60 and into the bone 62. The fastener 10 can be so advanced by advancing the pusher 48 distally advanced through the passageway 41, e.g., by actuating the first trigger 34 of the device 30, to slidably move the fastener 10 distally though the inner passageway 41 and out the distal end 40 of the cannula 38. The penetrating distal tip 14a of the first leg 12a can help advance the first leg 12a entirely through a depth 60d of the tissue 60 and into the bone 62, which can be harder than the tissue 60. As mentioned above, the pusher 48 can include one or more alignment marks which can help avoid under-insertion or over-insertion of the fastener 10 into the tissue 60 and/or the bone 62. For non-limiting example, when a first pusher alignment mark aligns with a corresponding mark on the cannula 38, thereby indicating that the fastener 10 has been advanced a predetermined distance distally far enough through the cannula 38 to move the first leg 12a out of the passageway 41, actuation of the pusher 48 can be manually stopped. Alternatively or in addition, the delivery device 30 can be configured to advance the fastener 10 a predetermined distance upon actuation of the first trigger 34, e.g., pulling the first trigger 34 once advances the fastener 10 a first predetermined distance. The device 30 can include a stop mechanism configured to provide a mechanical response, e.g., a "click," etc. after advancing the fastener 10 a predetermined distance beyond the distal end 40 of the cannula 38 to move the first leg 12a out of the passageway 41, which can also help ensure that the fastener 10 is advanced an appropriate distance out of the cannula 38 to move the first leg 12a into the tissue 60 and the bone 62. The second trigger 36 can be similarly configured.

Figure 12:
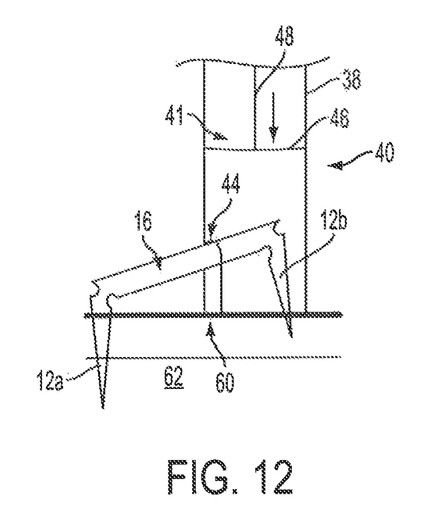
FIG. 12 is a 2 is a side, partially transparent view of the distal end of the surgical fastener delivery device cannula of FIG. 11 repositioned relative to the tissue with an intermediate portion of the surgical fastener of FIG. 11 extending through a window formed in the surgical fastener delivery device cannula.
Figure 13:
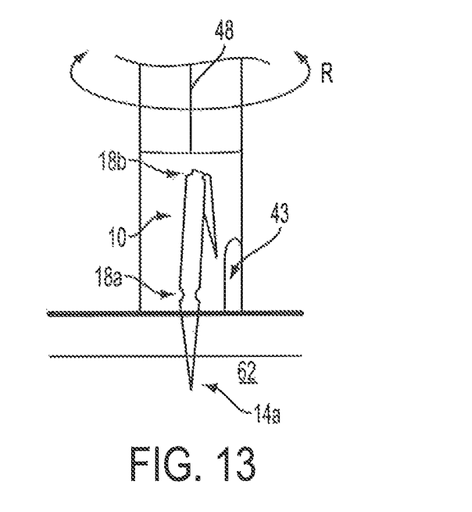
FIG. 13 is a side, partially transparent view of the distal end of the surgical fastener delivery device cannula of FIG. 12 being rotated about a longitudinal axis thereof.
Figure 14:
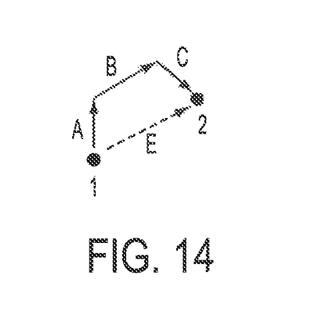
FIG. 14 is a schematic view of directions and locations in which a surgical delivery device cannula can be moved relative to tissue and bone.

After the first leg 12a is advanced, as illustrated in FIG. 12, the distal end 40 of the cannula 38 can be repositioned from the first location to a second location relative to the tissue 60 and the bone 62 with the first leg 12a advanced through the tissue 60 and into the bone 62, as shown in FIG. 12. The distal end 40 of the cannula 38 can be repositioned by moving the distal end 40 of the cannula 38 in a direction transverse to the longitudinal axis 38A of the cannula 38, e.g., laterally relative to the tissue 60 and the bone 62. As the distal end 40 of the cannula 38 moves from the first location, the second leg 12b of the fastener 10 can remain disposed within the passageway 41, and a partial longitudinal length of the backspan 16 of the fastener 10 can pass through the opening 43 formed in the distal end of the cannula 38. The first leg 12a advanced through the tissue 60 and into the bone 62 can serve as an anchor allowing the distal end 40 of the cannula 38 to be moved with the first leg 12a deployed from the cannula 38 and with another portion of the fastener 10 still disposed within the distal end 40 of the cannula 38. As the backspan 16 passes through the opening 43, the first leg 12a can pivot or bend relative to the backspan 16, e.g., pivot at the first joint 18a, and the second leg 12b can pivot or bend relative to the backspan 16, e.g., pivot at the second joint 18b. In other words, moving the cannula 38 laterally can cause the fastener 10 to move from the compressed configuration to the expanded configuration. As mentioned above, the first cut-outs 19a and/or a shape memory material of the fastener 10, e.g., at the first joint 18a, can facilitate such pivoting. During repositioning of the cannula 38, the backspan 16 can contact and be guided by the proximal end 44 of the opening 43, which can facilitate bending of the fastener 10.

To help ensure that the backspan 16 passes through the opening 43 instead of pressing against an interior wall of the passageway 41 and being prevented from exiting the passageway 41, the cannula 38 can be rotated about its longitudinal axis 38A to reposition the opening 43 relative to the fastener 10. The cannula 38 can be rotated clockwise and/or counterclockwise, as shown by directional arrow R in FIG. 13. The one or more alignment mechanisms of the cannula 38 can facilitate the rotation of the cannula 38 by allowing visual confirmation from outside the patient's body of the opening's position. One or more viewing devices within the patient's body can additionally or alternatively aid in positioning the opening 43 at a desired location relative to the fastener 10 after deploying the first leg 12a through the tissue 60 and into the bone 62. The cannula 38 be rotated any amount in any direction(s) at any time after the deploying the first leg 12a through the tissue 60 and into the bone 62. Because the second leg 12b has not yet been deployed into the tissue 60 or the bone 62, because the backspan 16 can extend through the opening 43, and because the cannula 38 can be rotated to reposition the opening 43 relative to the fastener 10, the cannula 38 can be moved laterally in any number of directions relative to the deployed first leg 12a, the tissue 60, and the bone 62 to guide the distal end 38 of the cannula 38 at an optimal second location relative to the tissue 60 and the bone 62. For non-limiting example, with reference to FIG. 14, with the first leg 12a deployed in the tissue and the bone 62 at a first location 1, the distal end 40 of the cannula 38 can be moved a first distance in a first direction A, a second distance in a second direction B, and a third distance in a third direction C to position the distal end 40 of the cannula 38 at a second location 2. At the first location 1 and/or at each of the two junctures between the different directions A, B and B, C, the cannula 38 can be rotated to reposition the opening 43 to allow the backspan 16 to extend through the opening 43 as the cannula 38 moves laterally. Alternatively, also with reference to FIG. 14, with the first leg 12a deployed in the tissue and the bone 62 at the first location 1, the distal end 40 of the cannula 38 can be moved a fourth distance in a fourth direction E to position the distal end 40 of the cannula 38 at a second location 2.

Figure 15:
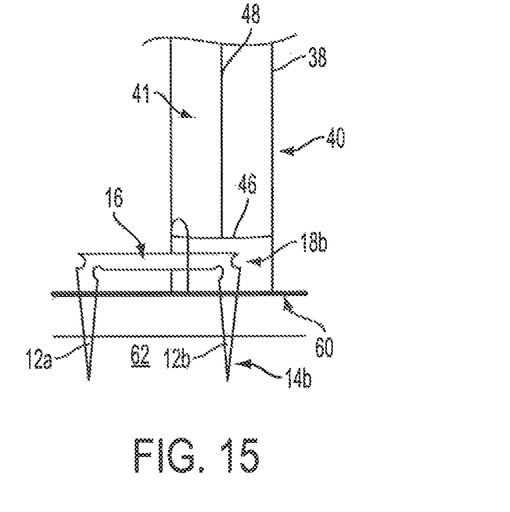
FIG. 15 is a side, partially transparent view of the pusher of FIG. 12 advancing a second leg of the surgical fastener of FIG. 12 out of the surgical fastener delivery device cannula of FIG. 12, through the tissue, and into the bone.

After the distal end 40 is repositioned at the second location, as shown in FIG. 15, the pusher 48 can be distally advanced to advance the second leg 12b of the fastener 10 distally though the passageway 41 and into the tissue 60 and into the bone 62, thereby delivering the fastener 10 and attaching the tissue 60 to the bone 62. Although the first and second cut-outs 19a, 19b are located proximal to a proximal surface of the tissue 60, and hence also proximal to a proximal surface of the bone 62 underlying the tissue 60, as shown in FIG. 15, a volume of the tissue 60 can be seated in one or both of the first and second cut-outs 19a, 19b to aid in retaining the fastener 10 in the tissue 60 and in the bone 62.

After the fastener 10 has been delivered, the cannula 38 and the pusher 48 can be removed from the patient, or one or more additional fasteners can be deployed using the device 30, e.g., by actuating the second trigger 36 to deploy a second fastener.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak)

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
   positioning a distal end of a cannula adjacent to a tissue overlying a bone;
   advancing a first leg of a fastener from the distal end of the cannula to drive the first leg through the tissue and into the bone;
   after advancing the first leg, repositioning the distal end of the cannula laterally relative to a longitudinal axis to the cannula and relative to the tissue; and
   after repositioning the distal end of the cannula, advancing a second leg of the fastener from the distal end of the cannula to drive the second leg through the tissue and into the bone, thereby attaching the tissue to the bone.

2. The method of claim 1, wherein repositioning the distal end of the cannula comprises moving the distal end of the cannula such that a back span of the fastener extending between the first and second legs pivots relative to the first leg.

3. The method of claim 1, wherein the fastener is formed from a shape memory material such that the back span is biased to pivot when the distal end of the cannula is repositioned relative to the tissue.

4. The method of claim 1, wherein advancing the first leg of the fastener comprises advancing the first leg of the fastener along the longitudinal axis of the cannula to pass the first leg of the fastener out of the cannula, and repositioning the distal end of the cannula comprises moving the cannula in a direction transverse to the longitudinal axis of the cannula.

5. The method of claim 1, wherein repositioning the distal end of the cannula causes an intermediate portion of the fastener extending between the first and second legs of the fastener to extend through an opening formed in a sidewall of the cannula.

6. The method of claim 1, wherein advancing the first leg of the fastener comprises driving a pusher distally through the cannula to push the first leg of the fastener through the tissue and into the bone, and advancing the second leg of the fastener comprises driving the pusher distally through the cannula to push the second leg of the fastener through the tissue and into the bone.

7. The method of claim 1, wherein repositioning the distal end of the cannula causes the first leg of the fastener to bend at a pre-formed joint of the fastener.

8. The method of claim 1, wherein repositioning the distal end of the cannula relative to the tissue comprises rotating the cannula relative to the fastener about a longitudinal axis of the cannula.

9. The method of claim 1, wherein the fastener includes a backspan extending between the first and second legs, the first leg being coupled to the backspan at a first pre-formed joint, the second leg being coupled to the backspan at a second pre-formed joint, the first and second pre-formed joints being formed from a shape memory material, and the first and second legs being formed from a non-shape memory material.

10. The method of claim 7, wherein the fastener has at least one of a cut-out formed in the fastener at the pre-formed joint and an interior channel defined by an interior surface of the pre-formed joint.

11. A surgical method, comprising:
    advancing a first end of a fastener longitudinally through an inner passageway of an elongate member to pass the first end out of the inner passageway, through a tissue of a patient, and into a bone underlying the tissue;
    after advancing the first end of the fastener, moving the elongate member laterally relative to the tissue, thereby moving a second end of the fastener located within the inner passageway laterally relative to the tissue and thereby causing an intermediate portion of the fastener extending between the first and second ends of the fastener to extend through an opening formed in a sidewall of the elongate member; and
    after moving the elongate member, advancing the second end of the fastener longitudinally through the inner passageway of the elongate member to pass the second end out of the inner passageway, through the tissue, and into the bone underlying the tissue.

12. The method of claim 11, wherein moving the elongate member laterally causes the intermediate portion to pivot such that the intermediate portion extends through the opening formed in the sidewall of the cannula.

13. The method of claim 11, further comprising, after advancing the second end of the fastener, removing the elongate member from the patient, thereby leaving the fastener implanted within the bone.

14. The method of claim 11, further comprising, after advancing the second end of the fastener, advancing a first end of a second fastener longitudinally through the inner passageway of the elongate member to pass the first end of the second fastener out of the inner passageway, through a tissue of a patient, and into a bone underlying the tissue;

after advancing the first end of the second fastener, moving the elongate member laterally relative to the tissue, thereby moving a second end of the second fastener located within the inner passageway to move laterally relative to the tissue and thereby causing an intermediate portion of the second fastener extending between the first and second ends of the second fastener to extend through the opening formed in the sidewall of the elongate member; and after moving the elongate member, advancing the second end of the second fastener longitudinally through the inner passageway of the elongate member to pass the second end of the second fastener out of the inner passageway, through the tissue, and into the bone underlying the tissue.

15. The method of claim 11, wherein advancing the first end of the fastener longitudinally comprises driving a pusher distally through the inner passageway of the elongate member to push the first end of the fastener through the tissue and into the bone, and advancing the second end of the fastener longitudinally comprises driving the pusher distally through the inner passageway of the elongate member to push the second end of the fastener through the tissue and into the bone.

16. The method of claim 11, wherein advancing the first end of the fastener longitudinally to push the first end of the fastener through the tissue and into the bone and advancing the second end of the fastener longitudinally to push the second end of the fastener through the tissue and into the bone causes the fastener to move from an initial substantially straight configuration to a final U-shaped configuration.

17. A surgical method, comprising:
   positioning a distal end of a cannula at a first position relative to a tissue overlying a bone, the cannula having a fastener disposed in a substantially linear configuration within an inner passageway of the cannula;
   after the positioning, advancing a first terminal end of the fastener longitudinally through the inner passageway to pass the first terminal end of the fastener out of the inner passageway, through the tissue, and into the bone;
   after advancing the first terminal end, moving the distal end of the cannula from the first position to a second position relative to the tissue, thereby causing the fastener to move from the substantially linear configuration to a bent configuration; and
   after moving the distal end of the cannula, advancing a second terminal end of the fastener longitudinally through the inner passageway of the cannula to pass the second terminal end of the fastener out of the inner passageway, through the tissue, and into the bone.

18. The method of claim 17, wherein moving the distal end of the cannula laterally causes an intermediate portion of the fastener extending between the first and second terminal ends of the fastener to extend through an opening formed in a sidewall of the cannula.

19. The method of claim 17, wherein moving the distal end of the cannula laterally causes an intermediate portion of the fastener extending between the first and second terminal ends of the fastener to move from a substantially longitudinal orientation to a substantially lateral orientation.

20. The method of claim 17, wherein the fastener is formed from a shape memory material such that the fastener is biased to move from the substantially linear configuration to the bent configuration when the distal end of the cannula is moved from the first position to the second position.

21. The method of claim 17, wherein the fastener in the bent configuration has a width that is greater than a diameter of the inner passageway of the cannula.

22. The method of claim 17, wherein the fastener has a substantially linear configuration between the first terminal end and the second terminal end.

* * * * *